United States Patent [19]

Aratani et al.

[11] Patent Number: 5,215,842
[45] Date of Patent: Jun. 1, 1993

[54] PHOTOSENSITIVE ELEMENT FOR ELECTROPHOTOGRAPHY

[75] Inventors: Sukekazu Aratani; Shigeo Suzuki; Akira Hosoya; Katuo Sugawara; Toshiro Saito, all of Hitachi; Tsuneaki Kawanishi, Tokai; Noriyuki Kinjo, Hitachi; Yasuo Katsuya, Hitachi; Akira Kageyama, Hitachi, all of Japan

[73] Assignees: Hitachi, Ltd.; Hitachi Chemical Co., Ltd., both of Tokyo, Japan

[21] Appl. No.: 638,544

[22] Filed: Jan. 8, 1991

[30] Foreign Application Priority Data

Jan. 8, 1990 [JP] Japan .......................................... 2-590

[51] Int. Cl.5 ............................................. G03G 5/06
[52] U.S. Cl. ........................................ 430/59; 430/73; 355/211
[58] Field of Search .................... 430/59, 73, 76, 77, 430/78; 355/211

[56] References Cited

U.S. PATENT DOCUMENTS 3,837,851  9/1974  Shattuck et al. .
3,871,882  3/1975  Wiedemann .
4,708,922 11/1987  Yokoya et al. ..................... 430/73
4,970,131 11/1990  Taniguchi et al. .................. 430/67

FOREIGN PATENT DOCUMENTS 092255  10/1983  European Pat. Off. ............. 430/59
52-072231  6/1977  Japan .
55-042380 10/1980  Japan .
57-195254 11/1982  Japan .
58-065440  4/1983  Japan .
59-075257  4/1984  Japan ................................. 430/59
60-008500  5/1985  Japan .
62-196666  8/1987  Japan .
2032637   5/1980  United Kingdom ................ 430/59

Primary Examiner—Marion E. McCamish
Assistant Examiner—Christopher D. RoDee
Attorney, Agent, or Firm—Antonelli, Terry, Stout & Kraus

[57] ABSTRACT

A photosensitive element for electrophotography has an electrically conductive substrate and a layer structure thereon comprising a charge generating substance and a charge transport substance. An improved charge transport substance is a derivative of triphenylamine in which at least 80% of the electrons in the highest occupied molecular orbital are located on the triphenylamine skeleton. Examples of such compounds have the following formula:

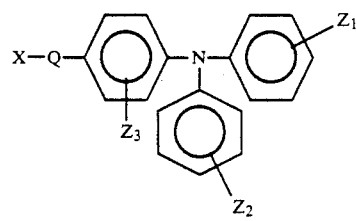

wherein X is a an optionally substituted heterocyclic radical containing at least one ring nitrogen, Q is a single bond or —C≡C—, and $Z_1$, $Z_2$ and $Z_3$ are H, lower alkyl or alkoxy, aryl, $NO_2$, $CF_3$, $-N(R')_2$, $-S-C_6H_5$ or $-S(R')_2$.

31 Claims, 2 Drawing Sheets

PHOTOSENSITIVE ELEMENT FOR ELECTROPHOTOGRAPHY

FIELD OF THE INVENTION

The present invention relates to a photosensitive element for electrophotography, and especially to a photosensitive element for electrophotography in the form of a drum or sheet, and to an electrophotographic apparatus including such an element, particularly an image forming device such as a photocopier, a laser printer and a facsimile-transmitting machine.

DESCRIPTION OF THE PRIOR ART

A photosensitive element for electrophotography to which the invention applies has a layer structure comprising a charge generation substance and a charge transport substance on a conductive substrate. The layer structure may comprise a homogeneous single layer including both the charge generating substance and the charge transport substance or a multi-layer structure comprising a layer containing the charge generation substance and a layer containing the charge transport substance. A charge transport substance is generally transparent and not absorbent to light having a specified range of wavelength for use in electrophotography, and is required to have the function to receive and to transport electrons injected from a charge generation substance. It is generally known that a photosensitive element having superior photoconductivity is obtained by using such a charge transport substance.

As charge transport substances which have such a function, photoconductive polymers such as polyvinyl carbazole etc. were proposed at first, but were insufficient in forming a film and commercialization was difficult. Therefore, many charge transport substances having low molecular weight which were used in dispersed state with a binder resin having a property to form a sufficient film have been proposed.

Among examples of the substances proposed, triaryl pyrazoline compounds are disclosed in JP-A-52-72231 (1977), hydrazone compounds are disclosed in JP-B-55-42380 (1980), and oxazole compounds are disclosed in JP-B-60-8500 (1985), and some of these compounds are used in practice. Nevertheless, image stability in long period usage which is required currently for a laser printer is not sufficient and an improvement is needed. In relation to the problems described above, chemical structures of charge transport substances and image stability have been studied. For example, a method of replacement of a dialkylamino group of the oxazole compounds with an arylamino group to improve the defect of oxazole compounds described above and to increase the image stability is disclosed in JP-A-62-96666 (1987). But, it is difficult to make image stability compatible with high sensitivity, and further improvement is required.

On the other hand, currently, a photosensitive element comprising multi-photosensitive layers which are divided functionally into charge generation layers and charge transport layers is proposed. Such an element has improved sensitivity for visible light, ability for keeping charge, and surface strength etc. (See U.S. Pat. No. 3,837,851 and U.S. Pat. No. 3,871,882. However, even with the multi-photosensitive layers, a photosensitive element for electrophotography having a conventional organic photoconductor as a charge transport substance layer has a problem that fluctuation of sensitivity and of electric potential at bright areas and dark areas may increase after repeated charges and exposures, and a resolution of this problem is required.

Some triphenylamine derivatives have been proposed as charge transport substances. JP-A-57-195254 (1982) discloses among many other compounds triphenylamine having one phenyl group substituted by phenyl. JP-A-58-65440 (1983) discloses triphenylamine derivatives in which one phenyl group is linked through the group —C=C— to aromatic radicals including

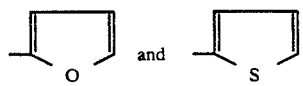

SUMMARY OF THE INVENTION

An object of the present invention is to provide a photosensitive element having a high sensitivity and superior image stability even after use for printing for a long time, with repeated charging and exposure, by overcoming at least partly the problems described above of known charge transport substances.

The present invention is based on the finding that some new compounds based on triphenylamine may be employed satisfactorily as charge transport substances, provided that certain principles are followed in selecting the structure of the compounds.

In one aspect the invention provides a photosensitive element for electrophotography having an electrically conductive substrate and a layer structure thereon comprising a charge generating substance and a charge transport substance, said charge transport substance being a derivative of triphenylamine in which at least 80% of the electrons in the highest occupied molecular orbital are located on the triphenylamine skeleton and having the following formula:

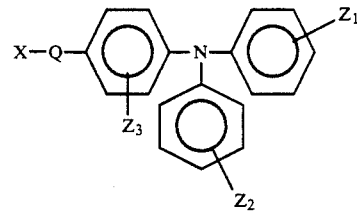

wherein
X is a heterocyclic radical containing at least one ring nitrogen and optionally substituted by a radical selected from the group consisting of lower alkyl, substituted lower alkyl, lower alkoxy, substituted lower alkoxy, aryl having 2 to 10 carbon atoms, substituted aryl having 2 to 10 carbon atoms, —$NO_2$, —$CF_3$, —$N(R)_2$, —S—$C_6H_5$ and —$S(R)_2$ wherein R is lower alkyl,
Q is selected from the group consisting of a single bond and —CH=CH—, and
each $Z_1$, $Z_2$ and $Z_3$ is selected from the group consisting of —H, lower alkyl, substituted lower alkyl, lower alkoxy, substituted lower alkoxy, aryl having 2 to 10 carbon atoms, substituted aryl having 2 to 10 carbon atoms, —$NO_2$, —$CF_3$, —$N(R')_2$, —S—$C_6H_5$ and —$S(R')_2$ wherein R' is lower alkyl.

In this specification and claims, "lower alkyl" and "lower alkoxy" mean radicals having 1 to 5 carbon atoms.

When the substituent group $Z_1$, $Z_2$ or $Z_3$ is itself substituted, the substituting group is for example —F, —Cl, —Br, —I or —$NO_2$.

The percentage of the electrons of the highest occupied molecular orbital located on the triphenylamine skeleton, which relates to the electron density distribution, is conveniently calculated by the well-known computer program-based MNDO method (Modified Neglect of Diatomic Orbital method) and specifically for the present invention the computer program MOPAC version 4.0 (QCPE No. 455) of QCPE (Quantum Chemistry Program Exchange) is employed.

The present inventors have found that there is a strong correlation between distribution of the electrons highest occupied molecular orbital in a charge transport material and drift rate thereof which is the factor determining optical response. Particularly in a triphenylamine derivative, the higher the electron concentration in the highest occupied molecular orbital on the triphenylamine skeleton, the higher is the drift rate thereof. Accordingly, by using such triphenylamine derivative as the electrical charge transport substance, an excellent photosensitive element for electrophotography can be provided.

The triphenylamine derivative used for the present invention in this aspect thereof is one in which molecular orbitals extend beyond the triphenylamine skeleton into at least one substituent thereof and in which more than 80%, preferably more than 85% of electrons in the highest occupied molecular orbital are located on the triphenylamine skeleton, i.e. the amino nitrogen and the three phenyl groups attached to it.

The heterocyclic radical X is normally at least partly conjugating with the triphenylamine skeleton. The ring nitrogen in the heterocyclic radical is preferably next to an unsaturated carbon (also in the radical) which is next to Q.

Particularly advantageous compounds are those in which more than 80% of electrons in the highest occupied molecular orbital locate on the triphenylamine skeleton and a heterocyclic radical is bonded to the triphenylamine skeleton via a carbon-carbon double bond.

More specifically, such a triphenylamine derivative may be represented by the following general formula:

$$(B—CH=CH)_n—A$$

wherein, A is a triphenylamine skeleton which may be substituted, B is a heterocycle which may be substituted, and n is an integer from 1 to 3.

As representative examples of such triphenylamine derivatives, the following compounds are enumerated; however, the present invention is not limited to these compounds.

The compounds represented by the following general formula are particularly advantageous:

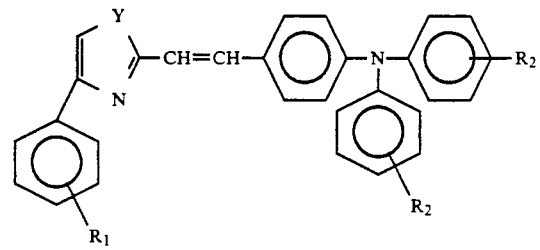

wherein, Y is O, S or NH, each $R_1$ and $R_2$ is hydrogen, lower alkyl, lower alkoxy, aryl group of $C_{2-10}$ which may include a substituent or dialkylamino group of $C_{2-20}$, and further $R_2$ and/or $R_3$ may be

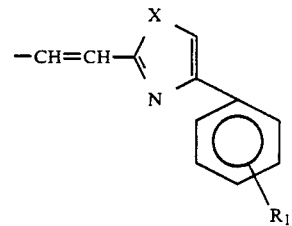

Specific examples of these compounds are as follows:

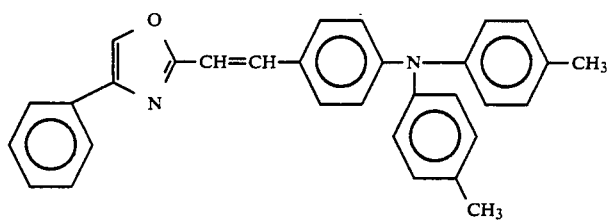

(a)

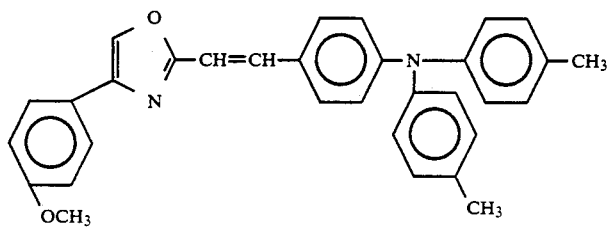

(b)

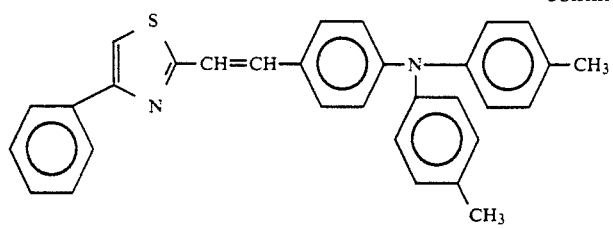
(c)
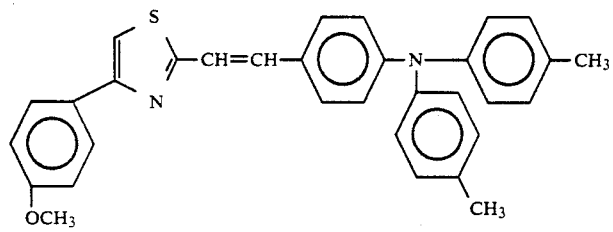
(d)
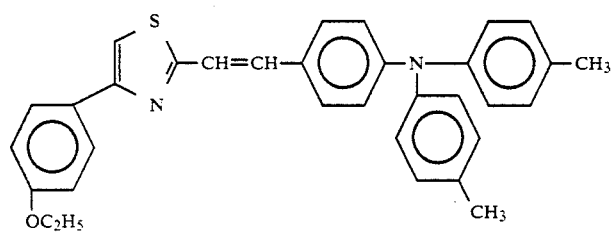
(e)
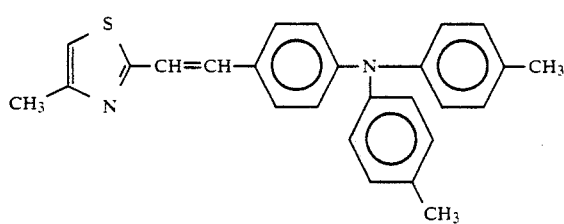
(f)
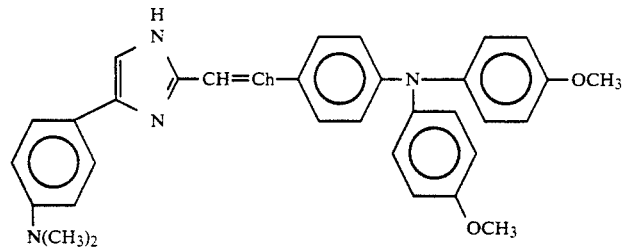
(g)
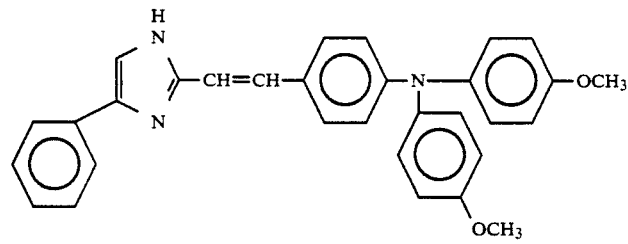
(h)
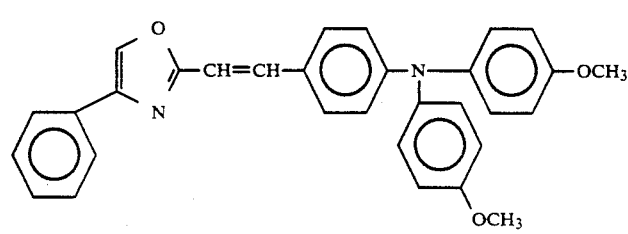
(i)

-continued
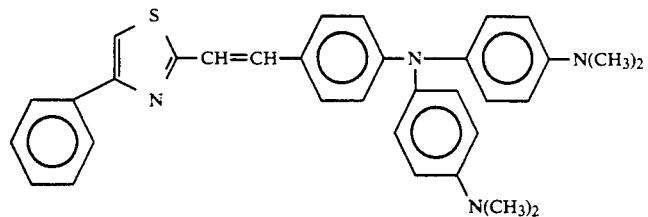 (j)
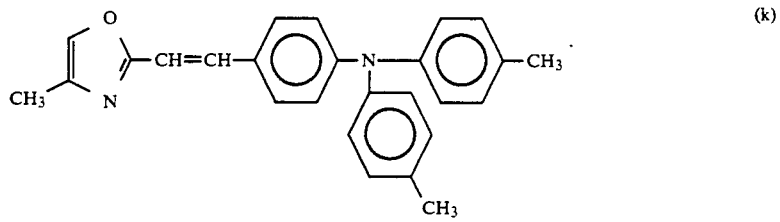 (k)
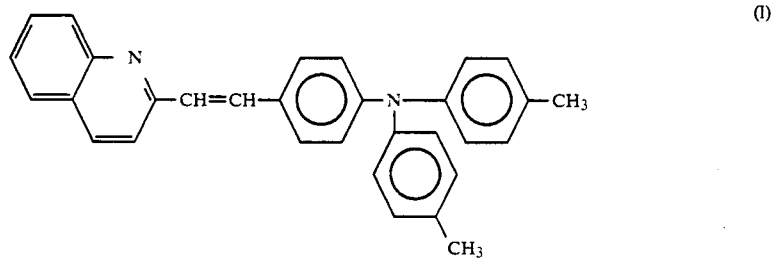 (l)
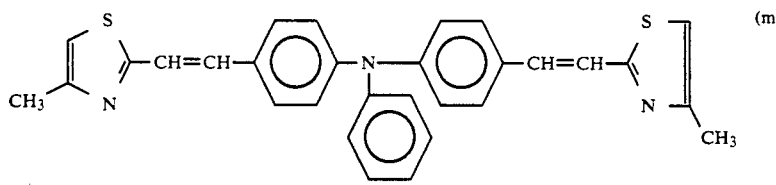 (m)
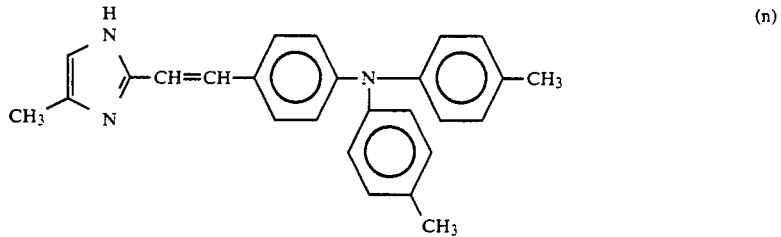 (n)
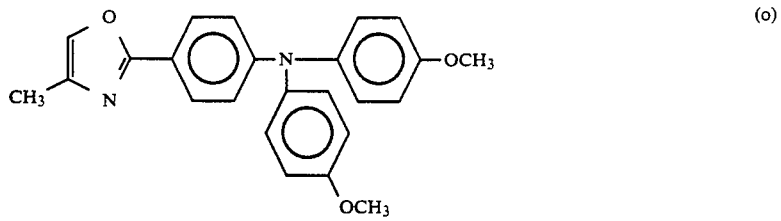 (o)
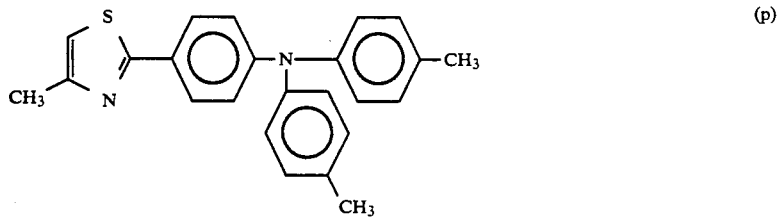 (p)
Although the reasons why these electrical charge transport compounds show a high drift rate have not Movement of electrical charge between electrical charge transport materials is performed via the highest occupied molecular orbital of respective molecules. Accordingly, electrons in the highest occupied molecular orbital preferably locate on a chemical structure which is likely to cause the movement of electrical charge. The triphenylamine is now thought to have such chemical structure so that the above tendency is considered to be obtainable.

In another aspect, the invention relates to certain new compounds based on triphenylamine having a styrylbenzene group joined to a heterocyclic group which have good sensitivity after usage for printing for a long time with repeated charge and exposure and good image stability. Again, without limitation by theory, it is considered that a compound having a conjugated system of $\pi$-electrons and a molecular structure wherein the structure configuration of the molecule is the one which makes the molecular structure difficult to be flattened is preferable as a charge transport substance and in addition attention must be paid to the effect of the substituent, for example the electron-withdrawing or electron-donating property thereof.

In this further aspect therefore, the invention provides a photosensitive element for electrophotography having an electrically conductive substrate and a layer structure thereon comprising a charge generating substance and a charge transport substance, said charge transport substance being a derivative of triphenylamine having the following formula:

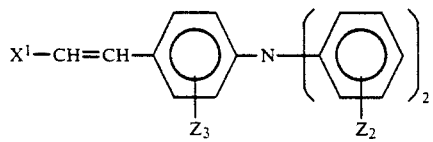

where X' is selected from the group consisting of

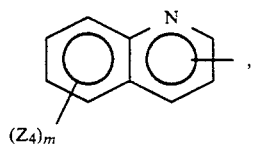

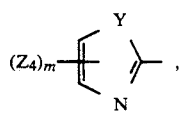

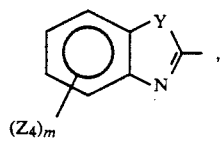

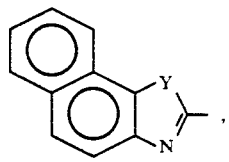

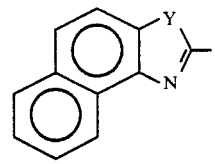

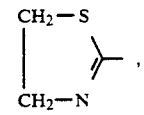

wherein m is selected from 1 and 2, Y is selected from the group consisting of —O—, —S—, —Se—, —NH—, —NR$_1$—, >CR$_2$R$_3$ wherein R$_1$ is lower alkyl and each of R$_2$ and R$_3$ is selected from —H and lower alkyl, and each of Z$_2$, Z$_3$ and Z$_4$ is selected from the group consisting of

—H lower alkyl optionally substituted by any of —F, —Cl, —Br, —I and —NO$_2$ lower alkoxy optionally substituted by any of —F, —Cl, —Br, —I and —NO$_2$, aryl having 2 to 10 carbon atoms optionally substituted by any of —F, —Cl, —Br, —I, —NO$_2$, lower alkyl and lower alkoxy,

—NO$_2$

—CF$_3$

—N(R)$_2$ where R is lower alkyl

—S—C$_6$H$_5$, and

—S(R')$_2$ where R' is lower alkyl.

In this general formula, particularly preferred forms of X' are

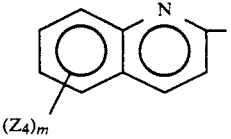

and

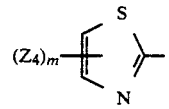

and particular examples of preferred structures are

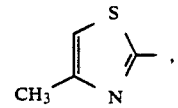

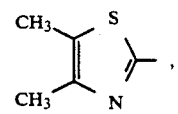

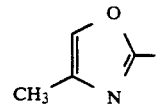

Particular examples of compounds within the invention in this aspect thereof are:

-continued
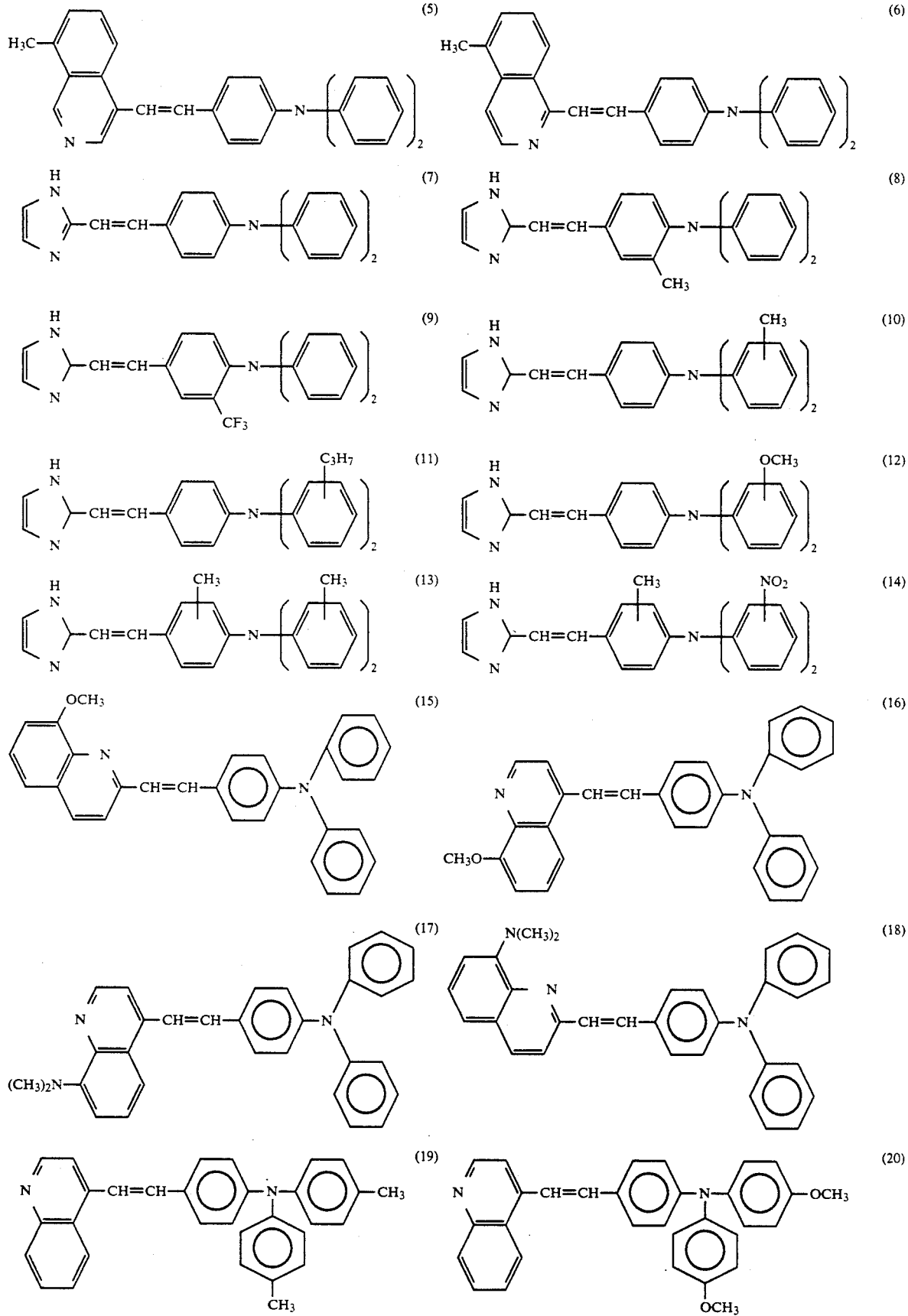

-continued
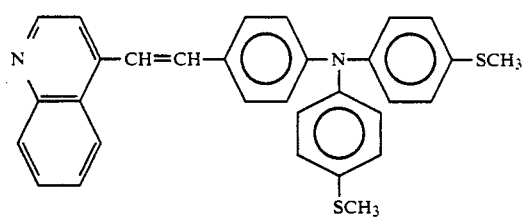 (21)
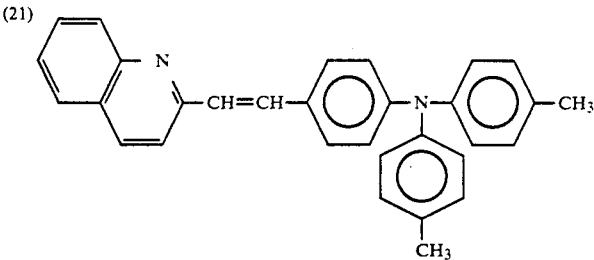 (22)
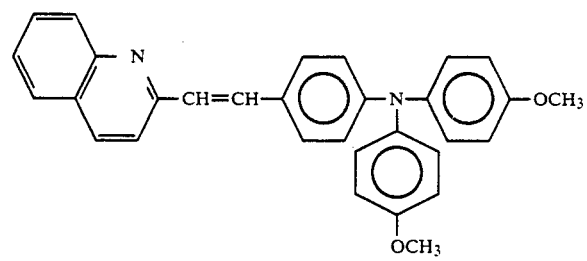 (23)
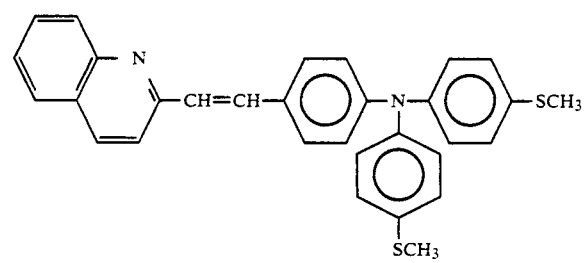 (24)
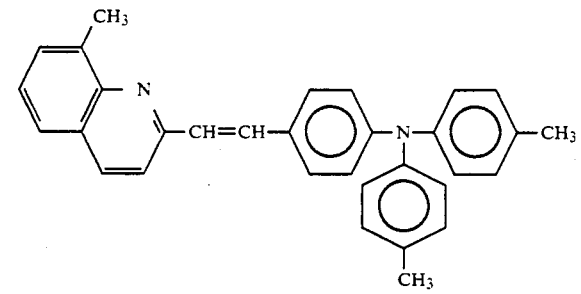 (25)
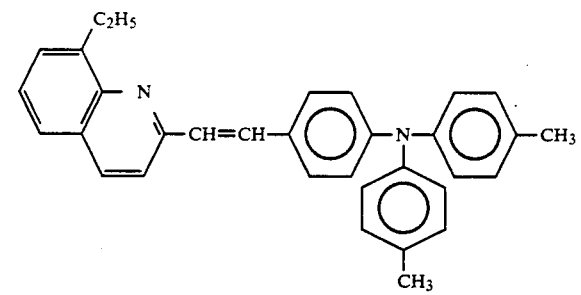 (26)
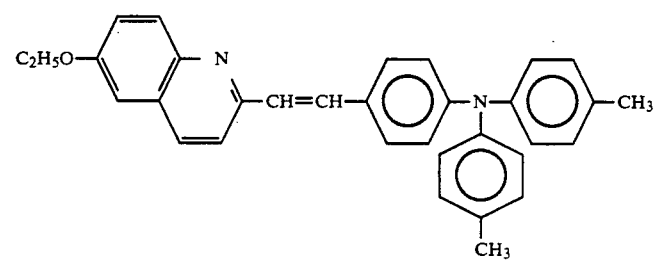 (27)

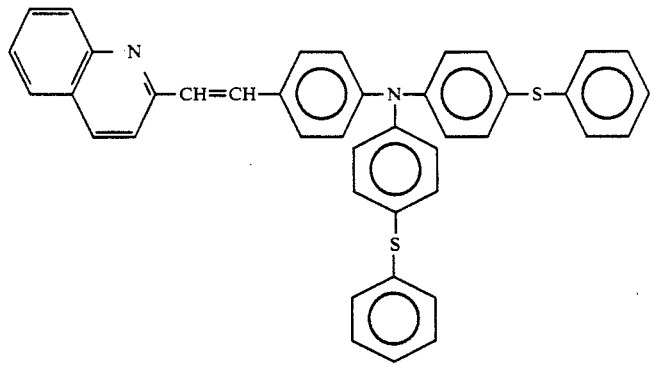

(28)

Preferably, in the compounds of this aspect of the invention, at least 80% of the electrons in the highest occupied molecular orbital are located on the triphenylamine skeleton.

In the present invention, the chemical compound which is the charge transport substance is usable as a mixture with a charge generation substance in a single layer, or in multi-layers. And even though a compound used in the present invention is able to form a charge transport layer by itself and be effective, it is possible to increase the effect by using a mixture with high polymer compounds for improvement of film strength, flexibility and adhesiveness.

The types of such high polymer compounds mentioned above are not restricted especially, and generally known bonding substances for an electrophotographical plate such as acrylic resin, butyral resin, polyester resin, polycarbonate resin, polyvinyl carbazole, melamine resin, urea resin, phenolic resin, epoxy resin, polyimide resin, or polyvinyl phenylanthracene etc. may be used. An appropriate mixing ratio of the high polymer compounds is within a range of 0.5 to 10 parts by weight to one part by weight of the charge transport compound.

As a charge generation substance in the present invention, conventional substances may be used, for example known organic pigments, dyes, charge transport complexes, compounds containing the phthalocyanine group, selenium and alloys containing selenium, cadmium sulfide, cadmium selenide, cadmium sulfoselenide, zinc sulfide, zinc oxide, and a mixture of such substances. In the present invention particularly preferred are oxotitanium (titanyl) phthalocyanine compounds and τ-form metal free phthalocyanine compounds.

As a conductive substrate or support in the present invention, metals such as aluminum, brass, gold, steel, copper, and other conductive materials, and high polymer compounds having a conductive coating may be used. Examples of such high polymer materials are polyethylene terephthalate (generally known Mylar film), polyamide film, polyimide film, polyether group film, polyketone group film etc. are usable. Such materials are usable in a sheet having an adequate thickness and hardness or flexibility, in a thin plate or in a cylindrical form, and when a metallic substance is used, a surface coating of the metallic substance with one of the high polymer substances described above or one of generally known high polymers may be used. Further, a metal coated paper, metal coated plastics sheet or aluminum iodide, copper iodide or chromium oxide, glass which is coated with a thin layer of indium oxide or tin oxide is usable. Generally, a substrate is conductive in itself, or has a conductive surface, and is preferably strong enough to be handled without special care.

BRIEF INTRODUCTION OF THE DRAWINGS

Embodiments of the invention will now be described by way of non-limitative example with reference to the accompanying drawings, in which:

FIGS. 1 to 7 each illustrate schematically a possible layer structure of an electrophotographic drum embodying the invention;

FIG. 8 illustrates schematically an electrophotographic sheet embodying the invention; and FIG. 9 is a diagrammatic view of an electrophotographic laser printer including a drum as illustrated in FIGS. 1 to 7.

DESCRIPTION OF THE PREFERRED EMBODIMENTS

Figure 1:
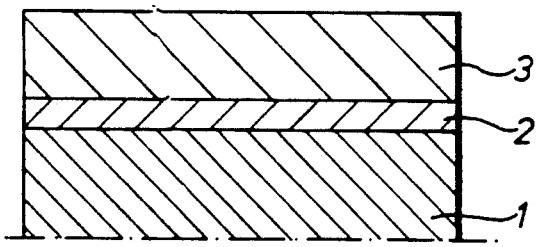
Figure 2:
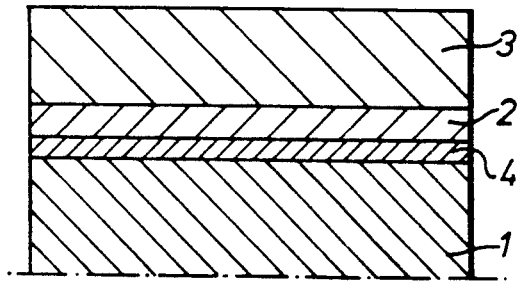
Figure 3:
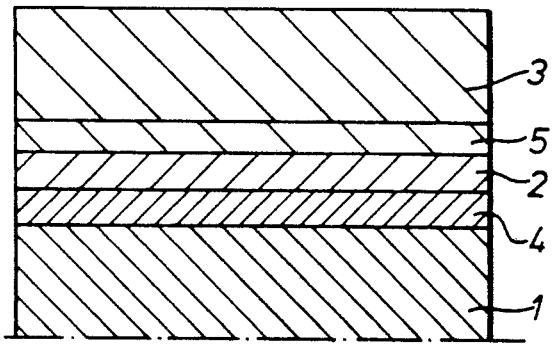
Figure 4:
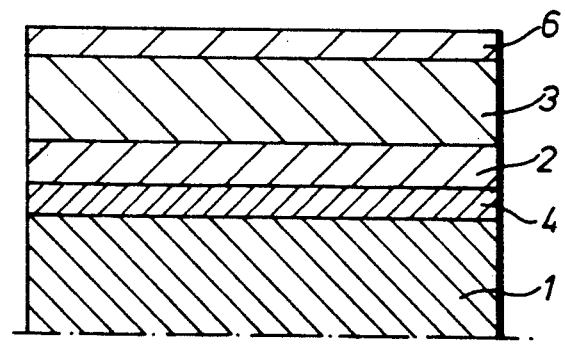

A photosensitive element of the present invention may have various layer structures, of which examples are illustrated in FIGS. 1 to 8. These figures schematically show the structure in section. Of course in practice, as in conventional devices, the shape and thickness of the layers is not as illustrated. FIGS. 1 to 4 show photosensitive layer structure comprising a charge generation substance layer 2 and a charge transport substance layer 3 formed directly onto a conductive substrate 1 (FIG. 1), a structure comprising a conductive substrate 1, a blocking layer 4 which is formed on the conductive substrate, and a charge generation layer 2 and a charge transport layer 3 formed on the blocking layer (FIG. 2), a structure comprising a layer 2 of a charge generation substance, a layer 3 of a charge transport substance, and an intermediate layer 5 which locates between these two layers, all on a blocking layer 4 and substrate 1 (FIG. 3), and a structure comprising a layer of protective film 6 on the surface of a structure as shown in FIG. 3 (FIG. 4).

Figure 5:
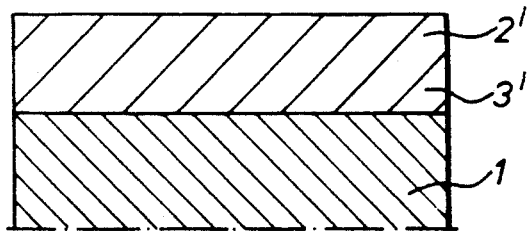
Figure 6:
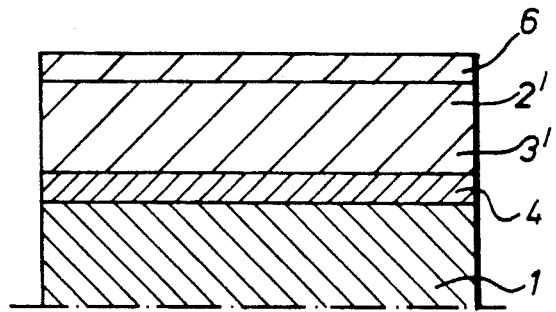
Figure 7:
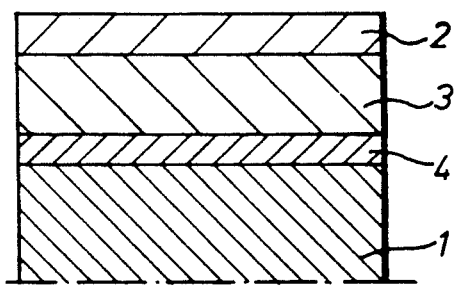
Figure 8:
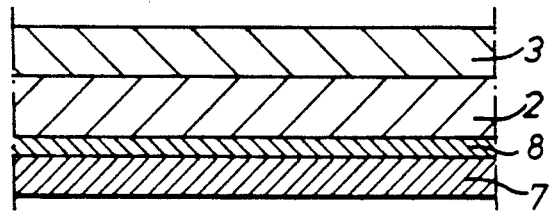

FIG. 5 shows a layer 2',3' containing charge generation substance and charge transport substance mixed, on a conductive substrate 1. FIG. 6 shows a similar layer 2',3' beneath a surface protective film 6 and separated from the substrate 1 by a blocking layer 4. FIG. 7 is the same as FIG. 3 but with the charge generating layer 2 and charge transport layer 3 reversed in order. FIG. 8 shows a flexible sheet photosensitive element consisting of, as substrate, an organic high polymer film 7 with a coating film 8 of aluminium formed by vacuum deposition, and charge generating layer 2 and charge transport layer 3 formed on the substrate.

The appropriate structure is selected in view of the intended use.

When using a coated high polymer film described above as a conductive substrate, the photosensitive body obtained is useful as a photosensitive sheet for use in electrophotography (FIG. 8).

In the present invention, the thickness of a layer or layers comprising a charge generation substance and a charge transport substance is determined essentially in dependence on charging characteristics which are necessary for the photosensitive element, but is preferably less than 100 μm. A layer having a thickness larger than 100 μm may decrease flexibility and photosensitivity of the layer. In the case of a single layer, the thickness is generally about 5-100 μm, while in the case of multilayers, it is adequate to use generally a thickness of about 0.1-5 μm for a charge generation layer and about 5-100 μm for a charge transport layer. Further, in the case of a single layer, the ratio of a charge generation substance to a charge transport substance is preferably about 10% by weight, but the ratio is optionally selected depending on the types and properties of the substances.

In the present invention, a blocking layer having a function as a barrier (to improve the charging property and to avoid unintentional exposure by preventing leakage of a charge to the conductive substrate) and a function as an adhesive can be formed between the conductive substrate and a photosensitive layer. For this blocking layer, polyamide resin, polyvinyl alcohol resin, polyurethane resin, aluminum oxide, etc. are among suitable materials.

In the present invention, an intermediate layer can be formed between a charge generation layer and a charge transport layer.

Referring back to the discussion above, explanation of some preferred compounds used in the invention can be given as follows. A charge transport substance is required to have (1) ease of carrier injection from a charge generation substance, (2) a superior carrier transport property, (3) stability against external conditions such as light and ozone, etc. To fulfil requirement (1), the ionization potential of the charge transport substance should preferably be nearly equal to the ionization potential of the charge generation substance, and if the ionization potential of the charge transport substance is too small, deterioration of the charge transport substance by light and ozone etc. occurs easily and the requirement (3) is not satisfied. Preferred chemical compounds used in the present invention have adequate ionization potential with a combination of the X—CH═CH— group and the aminoaryl group, and consequently, these chemical compounds are thought to fulfil requirements (1) and (3) concurrently.

To fulfil requirement (2), electrons of the highest occupied molecular orbital are preferably concentrated to a part which has a superior ability to transport carriers. The preferred chemical compounds used in the present invention have difficulty in taking a planar structure and have an arylamino group which has a superior ability of carrier transport, and further, requirement (2) is satisfied as the part X—CH═CH— concentrates electrons of the highest occupied molecular orbital to the arylamino group.

Non-limitative examples of embodiments of the present invention are described below, with synthesis examples.

SYNTHETIC EXAMPLE 1

A mixture of 11.4 g of quinaldine, 20.0 g of p-di (p-tolyl) aminobenzaldehyde and 5.0 g of zinc chloride anhydride was heated for 8 hours in an oil bath which was kept at 160°-170° C. and, subsequently, was dissolved into 100 ml of N, N-dimethylformamide, and, after addition of 10 ml of water and 20 ml of concentrated ammonium aqueous solution, an oily product was dissolved into 200 ml of benzene. The oily layer was washed several times with water, and after drying with magnesium sulfate, benzene was distilled off. The obtained oily product was purified twice by silica gel column chromatography using a benzene-ethylacetate mixture as eluent and after distilling off of the solvent, a residual oily component was recrystallized with methyl alcohol containing water, and 2-[p-di(p-tolyl)aminostyryl] quinoline (the above-illustrated compound 22) was obtained. The yield was 15.5 g, and the melting point of the compound was 130.5°-132.5° C.

EMBODIMENT 1

A solution for a charge generation layer was prepared by mixing by ball milling for five hours of one part by weight of τ form metal free phthalocyanine (Reophoton LS made by Toyo Ink Co.), two parts by weight of denatured silicone resin (KR-5221 made by Shinetsu Chemical Co., solid component 60%), and 37 parts by weight of tetrahydrofuran. The solution was applied to a thin aluminum foil 100 μm in thickness and 70×100 mm in size by an automatic applicator (made by Tokyo Seiki Co.) and, after drying for two hours at 130° C., a charge generation layer was obtained. The thickness of the layer was less than 1 μm.

Subsequently, a solution for a charge transport layer was obtained by dissolving five parts by weight of the product of Synthetic Example 1 (compound 22) and 10 parts by weight of polycarbonate resin (Lexan 141 made by General Electric Co.) into 84 parts by weight of a mixed solvent of methylene chloride/1,2-dichloroethane of 50/50 volume ratio. Using this solution, a charge transport layer was prepared on the charge generation layer by the same method as for the charge generation layer, and a photosensitive element was obtained. The thickness of the charge transport layer was about 20 μm.

Electrophotographical characteristics of this photosensitive element were measured with an apparatus for testing of electrostatic recording paper (SP-428 type made by Kawaguchi Electric Co.). The measurement included 10 seconds corona charging of −5 kV (the dynamic mode), 30 seconds standing in the dark, and subsequent exposure with a tungsten bulb. During the measurement, the electric potential on the surface of the photosensitive body was recorded and a voltage at the end of corona charging $V_0$, a voltage at the end of 30 seconds in the dark $V_{30}$, and a half-decay exposure $E_{50}$ (1×.s) were observed. The results were $V_0 = -1200$ V, $V_{30}/V_0 = 82\%$, and $E_{50} = 1.2$ 1×.s. Further, image stability was evaluated by the following deterioration test. A piece of specimen was bonded on the circumferential surface of a rotary drum which rotated at circumferential speed of 190 cm/minute and a process of charging with a corona charger which was installed near the drum with voltage of −5.2 kV during rotation and exposure with light of a tungsten lamp (illuminance 50 1×) which was installed at a direction of 180° from the corona charger was repeated for three hours. Subsequently, a resolution was evaluated by observing a resolution pattern which was obtained by contact exposure and development of a test chart published by the Society of Electrophotography (Tokyo) (No. 1-R, 1975 edition) with the naked eye.

The photosensitive element of Embodiment 1 showed no change in resolution which, when evaluated by the method described above after the deterioration test, was 12.5 lines/mm, comparing with an initial value of 12.5 lines/mm. When the electrophotographical characteristics were evaluated by the same method as at the initial stage of the deterioration test, the half decay exposure was 1.3 1×.s and significant change was not observed.

EMBODIMENTS 2-4

Instead of the charge transport substance used in Embodiment 1, the chemical compounds nos. (3), (4) and (9), were used for the preparation of photosensitive elements by the same method as Embodiment 1. The electrophotographic characteristics and resolution initially and after the deterioration test of the photosensitive bodies are shown in Table 1.

TABLE 1

| Embodiment | Compound No. | $V_0$ (−V) | $V_{30}/V_0$ (%) | $E_{50}$ (lx·s) | Resolution (lines/mm) |
|---|---|---|---|---|---|
| 2 | (3) | 1100 | 75 | 1.1 | 12.5 |
|   |     | 1120 | 76 | 1.1 | 12.5 |
| 3 | (4) | 1190 | 80 | 1.3 | 12.5 |
|   |     | 1190 | 81 | 1.4 | 12.5 |
| 4 | (9) | 1200 | 85 | 1.3 | 12.5 |
|   |     | 1210 | 85 | 1.3 | 12.5 |

For each embodiment, the upper line gives the initial results and the lower line the results after deterioration test.

EMBODIMENT 5

Using oxotitanium phthalocyanine (TOPA85 made by Toyo Ink. Co.) instead of the charge generation substance used in Embodiment 1, a photosensitive element was prepared by the same method as Embodiment 1. The initial electrophotographic characteristics measured by the same method as in Embodiment 1 were $V_0 = -1100$ V, $V_{30}/V_0 = 75\%$, $E_{50} = 1.2$ 1×.s, and the electrophotographic characteristics after the deterioration test were $V_0 = -1120$ V, $V_{30}/V_0 = 74\%$, $E_{50} = 1.2$ l.s, and significant change was hardly observed. The initial resolution was 12.5 lines/mm, and the resolution after the deterioration test was 12.5 lines/mm, and no change was observed.

EMBODIMENT 6

A solution for a blocking layer was prepared by dissolving 1.5 parts by weight of polyamide resin (M-1276 made by Nihon Rylsan Co.) and 1.5 parts by weight of melamine resin (ML-2000 made by Hitachi Chemical Co.) into a mixed solvent of 38.8 parts by weight of ethyl alcohol and 58.2 parts by weight of 1,1,2-trichloroethane. A thin aluminum foil 100 μm in thickness, 70×100 mm in size, was immersed into the coating liquid, and a blocking layer was prepared by withdrawing the foil from the coating liquid at a speed of 5 mm/second and drying for one hour at 120° C. On the surface of the blocking layer, a charge generation layer and a charge transport layer were prepared by the same method as Embodiment 5 and a photosensitive element was obtained.

The electrophotographical characteristics of the photosensitive body before and after the deterioration test were evaluated in the same way as in Embodiment 1. In the result, the electrophotographical characteristics were initially $V_0 = -1155$ V, $V_{30}/V_0 = 80\%$, $E_{50} = 1.3$ 1×.s, and the resolution was 12.5 lines/mm. After the deterioration test, $V_0 = -1170$V, $V_{30}/V_0 = 80\%$, $E_{50} = 1.3$ 1×.s, and resolution 12.5 lines/mm. No significant change was observed.

SYNTHETIC EXAMPLE 2

A mixture of 10.0 g of quinaldine, 19.0 g of p-diphenylaminobenzaldehyde and 5.0 g of zinc chloride anhydride was heated for 8 hours in an oil bath which was kept at 160–170° C. and subsequently the mixture was dissolved into 100 ml of N,N-dimethylformamide, and, after adding 10 ml of water and 20 ml of concentrated ammonium aqueous solution, an oily product was dissolved into 200 ml of benzene. The organic layer was washed several times with water and, after drying with magnesium sulfate, benzene was distilled off. The obtained oily product was purified twice with silica gel column chromatography using a benzene-ethylacetate mixture as eluent, and after distilling off of the solvent, a residual oily component was recrystallized with methyl alcohol containing water, and 2-(p-diphenyl aminostyryl) quinoline illustrated below was obtained. The yield was 5.7 g, and the melting point of the compound was 153.5°–154.5° C.

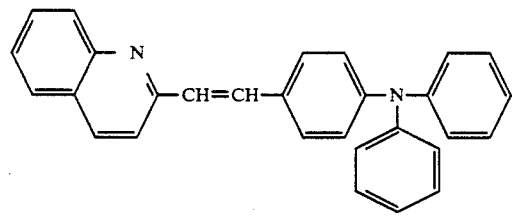

SYNTHETIC EXAMPLE 3

Using 10.0 g of lepidine and 19.0 g of p-diphenylaminobenzaldehyde, 4-(p-diphenylaminostyryl) quinoline illustrated below was obtained by the same method as Synthetic Example 1. They yield was 6.9 g, and the melting point was 92.0°–95.0° C.

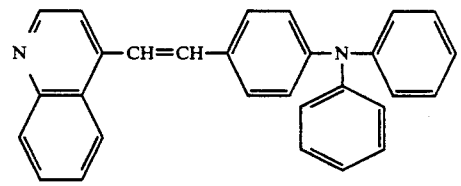

SYNTHETIC EXAMPLE 4

Using 17.0 g of lepidine and 30.0 g of p-di (p-tolyl) aminobenzaldehyde, 4-[p-di (p-tolyl) aminostyryl] quinoline illustrated below was obtained by the same method as Synthetic Example 1. The yield was 17.0 g, and the melting point was 90.5°–93.° C.

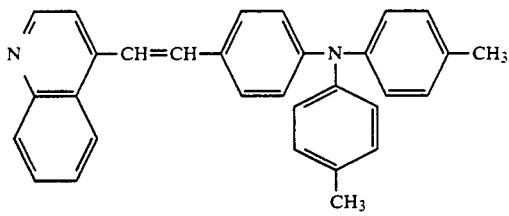

SYNTHETIC EXAMPLE 5

Using 5.4 g of 2,4-dimethylthiazole and 12.0 g of p-di (p-tolyl) aminobenzaldehyde, 2-[p-di (p-tolyl) aminostyryl] 4-methylthiazole illustrated below was obtained by the same method as Synthetic Example 1. The yield was 3.6 g, and the melting point was 100.0°-102.0° C.

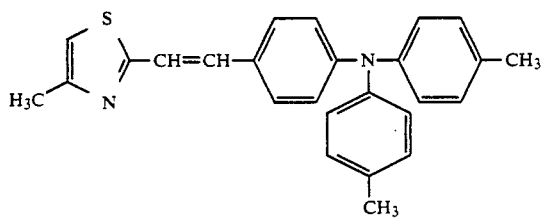

EMBODIMENT 7

A solution for a charge generation layer was prepared by ball milling for about 5 hours admixture of one part by weight of oxotitanium phthalocyanine, two parts by weight of denatured silicone resin (KR-5221 made by Shinetsu Chemical Co., solid content 60%), and 37 parts by weight of tetrahydrofuran. A charge generation layer was prepared by applying the solution described above to a thin aluminum foil of 100 μm thickness with an automatic applicator (made by Tokyo Seiki Co.) and dried for two hours at 130° C. The thickness of the layer was less than 1 μm.

Subsequently, a solution for a charge transport layer was obtained by dissolving five parts by weight of the chemical compound of Synthetic Example 1, that is 2-[p-di(p-tolyl) aminostyryl] quinoline, and 10 parts by weight of polycarbonate resin (Lexan 141 made by General Electric Co.) to 84 parts by weight of a mixed solvent of methylene chloride /1,2-dichloroethane=50/50 by weight. Using this solution, a charge transport layer was prepared on the charge generation layer by the same method as the charge generation layer, and a photosensitive element was obtained. The thickness of the charge transport layer was about 20 μm.

Electrophotographical characteristics of the photosensitive body described above were measured by the test methods of Embodiment 1. The results were $V_0 = -1210$ V, $V_{30}V_0 = 83\%$, and $E_{50} = 1.3$ 1×.s. Further, image stability was evaluated by the deterioration test of Embodiment 1. The photosensitive element showed no change in resolution after the deterioration test, that was 12.5 lines/mm, comparing with an initial value of 12.5 lines/mm. After the deterioration test, the half decay exposure $E_{50}$ was 1.3 1×.s and no significant change wa observed.

EMBODIMENTS 8-10

Using chemical compounds obtained in the synthetic Examples 3, 4, 5 and 6, instead of the charge transport substance in Embodiment 7, photosensitive elements were prepared and tested by the same methods as in Embodiment 7. Electrophotographic characteristics and resolution initially and after the deterioration test of the photosensitive elements for electrophotography of these embodiments are shown in Table 2.

TABLE 2

| Embodiment | Synthetic example compound | $V_0$ (−V) | $V_{30}/V_0$ (%) | $E_{50}$ (lx · s) | Resolution (lines/mm) |
| --- | --- | --- | --- | --- | --- |
| 8 | 3 | 1080 | 78 | 1.7 | 12.5 |
|   |   | 1080 | 79 | 1.8 | 12.5 |
| 9 | 4 | 1190 | 80 | 1.3 | 12.5 |
|   |   | 1190 | 81 | 1.4 | 12.5 |
| 10 | 5 | 1200 | 85 | 1.3 | 12.5 |
|   |   | 1210 | 85 | 1.3 | 12.5 |

For each embodiment, the upper line gives the initial results and the lower line the results after deterioration test.

These embodiments show that the present invention can provide a superior photosensitive element for electrophotography which shows scarcely any deterioration in sensitivity and image stability even after repeated charging and exposure over long periods by using new chemical compound having a triarylamine group as a charge transport substance.

SYNTHETIC EXAMPLE 6

By using 14 g of 6-methylquinaldine and 25 g of p-di(p-tolyl)aminobenzaldehyde and in the same manner as in Synthetic Example 1 the compound 2-[p-di(p-tolyl)aminostyryl]-6-methylquinoline was obtained. The yield was 24 g and the melting point thereof was 200°-202.5° C. This compound may also be used satisfactorily as a charge transport substance.

EMBODIMENT 11

A solution for a blocking layer was prepared by dissolving 2.0 parts by weight of polyamide resin (H-104, product of Nihon Rylsan Co.) and 0.5 parts by weight of melamine resin (Melan-200, product of Hitachi Chemical Co.) into 100 parts by weight of a 1/1 (by weight) mixture solvent of 1,1,2 trichloroethane/ethanol. A thin aluminum sheet having a thickness of 0.1 μm was immersed into the coating liquid to coat the same, and thereafter the coated sheet was dried by heating at 120° C. for 30 minutes to obtain a blocking layer having a thickness of about 0.2 μm. Next, a solution for an electrical charge generating layer was prepared by kneading with a ball mill for about 5 hours 1 part by weight of τ-type phthalocyanine (Reophoton LS, product of Toyo Ink Co.), 2 parts by weight of denatured silicon resin (KR-5221, product of Shinetsu Chemical Co., solid component 60%), and 37 parts by weight of tetrahydrofuran. The resultant solution was applied over the blocking layer prepared previously with an automatic applicator (product of Toyo Seiki Co.) and the coated sheet was dried at 130° C. for 2 hours to obtain an electrical charge generating layer.

Subsequently, a solution for an electrical charge transport layer was obtained by dissolving 5 parts by weight of the compound indicated in the above lists as (d) and 10 parts by weight of polycarbonate resin (Lexan 141, product of General Electric Co.) into 84 parts of a 50/50 (by volume ratio) solvent mixture of methylene chloride/1,2-dichloroethane. By using the resultant solution, an electrical charge transport layer was formed over the electrical charge generating layer in the same manner as in the formation of the electrical charge generating layer and a photosensitive element of the structure shown in FIG. 1 was obtained. The film thickness of the charge transport layer was about 20 μm.

Electrophotographic characteristics of the above photosensitive element were measured in the same manner as in Embodiment 1. The results were $V_0 = -1100$ V, $V_{30}/V_0 = 0.90$, and $E_{50} = 1.1$ 1×.s.

Thereafter, for evaluating optical response property the following experiment was performed. The specimen was corona charged with a high speed light decay measurement apparatus (CYNTHIA 30HL, product of Gentic Co.) until the surface potential of the specimen photosensitive substance reached $-700$ V, and the specimen was irradiated with a light beam having a wavelength of 780 nm and a light power of 40 mJ/m² for 40 msec and the half decay exposure time $t_{50}$ until the surface voltage is reduced to half was measured to obtain a value $t_{50} = 18$ ms.

The percentage of electrons in the highest occupied molecular orbital of the compound (d) which locate on the triphenylamine skeleton was calculated by the MNDO method defined above and found to be 91.4%.

Subsequently, the durability of this element was evaluated by the deterioration test described in Embodiment 1, in which the photosensitive element of the present embodiment showed no change, in that the resolution was initially 12.5 lines/mm and after the deterioration test was also 12.5 lines/mm. Further, after the deterioration test, the electrophotographic characteristics of the specimen was evaluated in the same manner as initially and was found out that no change was observed in the half decay exposure amount, in that it was 1.1 1×.s.

EMBODIMENT 12

In place of the compound (d) used in Embodiment 11 the compound produced by Synthetic Example 3 was employed for the electrical charge transport material, and a photosensitive element was prepared in the same manner as in Embodiment 11. Electron distribution in the highest occupied molecular orbital of the present compound was calculated by making use of the MNDO method as defined above, and the percentage of electrons locating on the triphenylamine skeleton was found to be 75.2%. The electrophotographic characteristics and optical response properties of this photosensitive element were evaluated as in Embodiment 11. The results were $V_0 = -1150V$, $V_{30}/V_0 = 0.91$, $E_{50} = 1.5$ 1×.s, $t_{50} = 40$ ms.

Furthermore, the electron distribution in the highest occupied molecular orbital of the compound A-(19) disclosed in JP-A-58-65440 (1983) on page 270, second column was calculated. The electron location rate on the triphenylamine skeleton was 71.8%.

EMBODIMENTS 13-21

In place of the electrical charge transport material used in Embodiment 11, nine of the compounds illustrated above were employed in the manufacture of photosensitive elements in the same manner as in Embodiment 11. Table 3 respectively shows initial values (upper line for each compound) and values after the deterioration test (lower line for each compound) of electrophotographic characteristics, optical response property and resolution of these photosensitive elements and the rate D at which electrons in the highest occupied molecular orbital locate on the triphenylamine skeleton of the compound. In Table 3 the first column is the embodiment number and the second column indicates the illustrated compound

TABLE 3

|    |     | D (%) | $V_0$ ($-V$) | $V_{30}/V_0$ | $E_{50}$ (lx · s) | $t_{50}$ (ms) | Resolution (line/mm) |
|----|-----|-------|--------------|--------------|-------------------|---------------|----------------------|
| 13 | (b) | 85.5  | 1100         | 0.91         | 1.1               | 18.0          | 12.5                 |
|    |     |       | 1120         | 0.92         | 1.1               | 18.0          | 12.5                 |
| 14 | (f) | 81.8  | 1110         | 0.89         | 1.1               | 20.0          | 12.5                 |
|    |     |       | 1130         | 0.90         | 1.09              | 20.0          | 12.5                 |
| 15 | (k) | 82.0  | 1115         | 0.90         | 1.11              | 19.5          | 12.5                 |
|    |     |       | 1130         | 0.92         | 1.10              | 19.5          | 12.5                 |
| 16 | (l) | 80.8  | 1140         | 0.92         | 1.15              | 22.5          | 12.5                 |
|    |     |       | 1160         | 0.93         | 1.20              | 23.0          | 12.5                 |
| 17 | (p) | 81.5  | 1130         | 0.92         | 1.10              | 21.0          | 12.5                 |
|    |     |       | 1140         | 0.93         | 1.11              | 21.0          | 12.5                 |
| 18 | (c) | 80.0  | 1120         | 0.90         | 1.20              | 20.0          | 12.5                 |
|    |     |       | 1100         | 0.89         | 1.18              | 20.0          | 12.5                 |
| 19 | (e) | 90.0  | 1100         | 0.91         | 1.14              | 19.0          | 12.5                 |
|    |     |       | 1050         | 0.85         | 1.12              | 18.5          | 12.5                 |
| 20 | (m) | 82.0  | 1060         | 0.90         | 1.20              | 20.0          | 12.5                 |
|    |     |       | 1000         | 0.86         | 1.20              | 20.0          | 12.5                 |
| 21 | (o) | 81.1  | 1020         | 0.89         | 1.23              | 21.0          | 12.5                 |
|    |     |       | 1000         | 0.87         | 1.22              | 21.0          | 12.5                 |

Further the respective values D for the illustrated compounds (a), (g), (h), (i), (j) and (n) were calculated to be 80.2%, 80.5%, 84.5%, 87.0%, 82.0% and 82.5% respectively, and these compounds also exhibited excellent electrophotographic characteristics.

EMBODIMENT 22

In the same manner as in Embodiment 11, a photosensitive element was prepared using oxotitaniumphthalocyanine for the electrical charge generating material. The electrophotographic characteristics, optical response property and resolution of this photosensitive element were evaluated in the same way before and after the deterioration test. The initial electrophotographic characteristics and optical response property were $V_0 = -1100V$, $V_{30}/V_0 = 0.86$, $E_{50} = 1.09$ 1x.s, $t_{50} = 18.0$ ms, and the resolution 12.5 lines/mm and after the deterioration test the electrophotographic characteristics, and optical response property were $V_0 = -1120V$, $V_{30}/V_0 = 0.89$, $E_{50} = 1.10$ 1x.s, and $t_{50} = 18.0$ ms and the resolution was 12.5 lines/mm.

EMBODIMENT 23

A photosensitive element was prepared by subsequently laminating an electrical charge generating layer and an electrical charge transport layer on a sheet of Mylar film on which aluminum was evaporated, in the same manner as in Embodiment 11. Before and after the deterioration test the electrophotographic characteristics, optical response property and resolution of this photosensitive element were evaluated in the same way. The initial electrophotographic characteristics and optical response property were $V_0 = -1050V$, $V_{30}/V_0 = 0.84$, $E_{50} = 1.09$ 1x.s, $t_{50} = 18.0$ ms, and the resolution was 12.5 lines/mm. After the deterioration test, the results were $V_0 = -1070$ V, $V_{30}/V_0 = 0.86$ $E_{50} = 1.10$ 1x.s. $t_{50} = 18.0$ ms and the resolution was 12.5 lines/mm.

EMBODIMENT 24

A solution for a surface protective layer was prepared of 60 parts by weight of butyl etherealized melamine formaldehyde resin, 40 parts by weight of isopropylalcohol and 0.03 parts by weight of silane coupling agent, and was applied to the photosensitive element of Embodiment 11 in the same manner as was used for forming the electrical charge transport layer, and was cured at 120° C. to obtain a photosensitive element provided with a protective layer. Before and after the same deterioration test, the electrophotographic optical response property and resolution of this photosensitive element were evaluated in the same way. The initial electrophotographic characteristics and optical response property were $V_0 = -1150$ V, $V_{30}/V_0 = 0.95$, $E_{50} = 1.15$ lx.s, $t_{50} = 19.0$ ms and the resolution was 12.5 lines/mm. After the deterioration test the results were $V_0 = -1160$ V, $V_{30}V_0 = 0.96$, $E_{50} = 1.16$ lx.s and $t_{50} = 19.0$ ms and the resolution was 12.5 lines/mm.

EMBODIMENT 25

In the same manner as in Embodiment 11, a photosensitive layer structure was formed on a bare aluminum cylinder. This photosensitive drum was loaded into an electrophotographic device having the constitution as shown in FIG. 9 and tested, and even after output of 100,000 prints of A4 size, an excellent picture image print was obtained.

Figure 9:
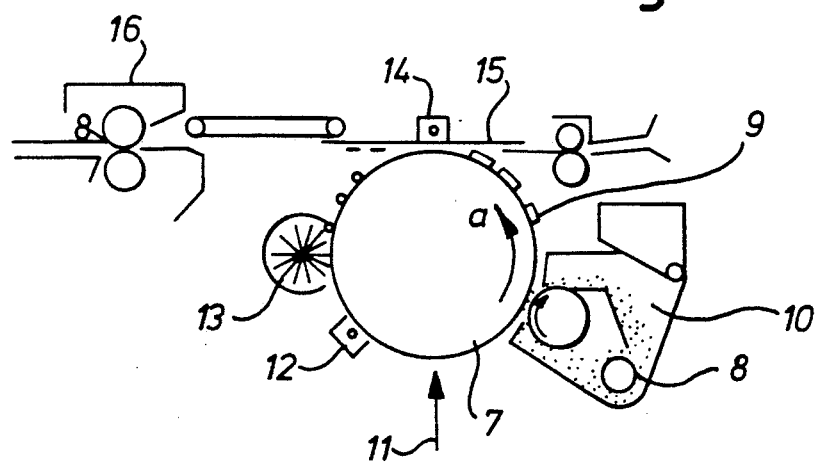

FIG. 9 shows a laser printer having a photosensitive drum 7, a developing device 10 applying developing agent 8 to the drum, a corona discharge charger 12 and a fur brush 13 for cleaning the drum. Paper 15 is moved past an image transfer device 14 at the drum to a fixing device 16. In operation, the drum 7 is charged by the charger 12, given an electrostatic image by the laser beam 11, toner is applied by developing device 10 to give a toner image 9, which is transferred to the paper by transfer device 14 and fixed. Such apparatus is generally known and need not be described further.

Electrophotographic apparatuses according to the invention employ photosensitive elements which can have excellent response and high durability. Excellent image printing can be achieved, and maintenance requirements can be reduced.

What is claimed is:

1. A photosensitive element for electrophotography having an electrically conductive substrate and a layer structure thereon comprising a charge generating substance and a charge transport substance, said charge transport substance being a derivative of triphenylamine in which at least 80% of the electrons in the highest occupied molecular orbital are located on the triphenylamine skeleton and having the following formula:

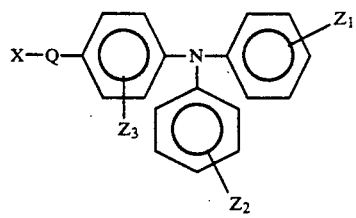

wherein

X is a heterocyclic radical containing a single ring nitrogen atom, said heterocyclic radical being optionally substituted by a radical selected from the group consisting of lower alkyl, lower alkoxy, aryl having 6 to 10 carbon atoms, $-NO_2$, $-CF_3$, $-N(R)_2$, $-S-C_6H_5$ and $-S(R)_2$ wherein R is lower alkyl;

Q is $-CH=CH-$; and each $Z_1$, $Z_2$, and $Z_3$ is selected from the group consisting of $-H$, lower alkyl, lower alkoxy, aryl having 6 to 10 carbon atoms, $-NO_2$, $-CF_3$, $-N(R')_2$, $-S-C_6H_5$ and $-S(R')_2$ wherein R' is lower alkyl.

2. A photosensitive element according to claim 1 wherein said ring nitrogen in said heterocyclic radical is next to an unsaturated carbon atom which is next to Q.

3. A photosensitive element according to claim 1 wherein said layer structure comprises a first layer containing said charge generating substance and a second layer more remote from said substrate than said first layer containing said charge transport substance.

4. A photosensitive element according to claim 1 wherein said layer structure comprises a layer containing said charge generating substance and said charge transport substance mixed.

5. A photosensitive element according to claim 1 further comprising a blocking layer lying between said layer structure containing said charge generating substance and said charge transport substance and said substrate.

6. A photosensitive element according to claim 1 wherein said layer structure comprises a charge transport layer containing said charge transport substance and a protective surface layer.

7. A photosensitive element according to claim 6 wherein said protective surface layer also contains said charge transport substance.

8. A photosensitive element according to claim 1 wherein said charge generating substance is a phthalocyanine compound.

9. A photosensitive element according to claim 1 which is in sheet form and wherein said substrate comprises a polymeric support sheet and a conductive thin film thereon.

10. Electrophotographic apparatus including at least one photosensitive element according to claim 1.

11. A photosensitive element for electrophotography having an electrically conductive substrate and a layer structure thereon comprising a charge generating substance and a charge transport substance, said charge transport substance being a derivative of triphenylamine in which at least 80% of the electrons in the highest occupied molecular orbital are located on the triphenylamine skeleton and in which a heterocyclic radical containing a single ring nitrogen atom is attached to said triphenylamine skeleton via a carbon-carbon double bond.

12. A photosensitive element according to claim 11 wherein said heterocyclic radical contains a ring nitrogen next to an unsaturated carbon atom which is joined directly to said triphenylamine skeleton via the group $-C=C-$ which provides said carbon-carbon double bond.

13. A photosensitive element according to claim 11 wherein said layer structure comprises a first layer containing said charge generating substance and a second layer more remote from said substrate than said first layer containing said charge transport substance.

14. A photosensitive element according to claim 11 wherein said layer structure comprises a layer containing said charge generating substance and said charge transport substance mixed.

15. A photosensitive element according to claim 10 further comprising a blocking layer lying between said layer structure containing said charge generating substance and said charge transport substance and said substrate.

16. A photosensitive element according to claim 11 wherein said layer structure comprises a charge transport layer containing said charge transport substance and a protective surface layer.

17. A photosensitive element according to claim 16 wherein said protective surface layer also contains said charge transport substance.

18. A photosensitive element according to claim 11 wherein said charge generating substance is a phthalocyanine compound.

19. A photosensitive element according to claim 11 which is in sheet form and wherein said substrate comprises a polymeric support sheet and a conductive thin film thereon.

20. Electrophotographic apparatus including at least one photosensitive element according to claim 11.

21. A photosensitive element for electrophotography having an electrically conductive substrate and a layer structure thereon comprising a charge generating substance and charge transport substance, said charge transport substance being a derivative of triphenylamine having the following formula:

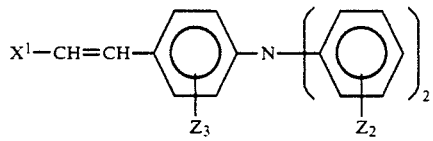

wherein X' is selected from the group consisting of

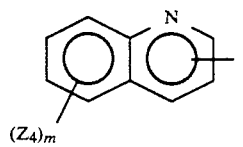

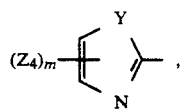

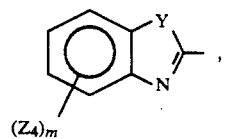

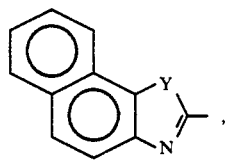

-continued

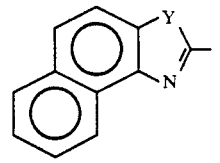

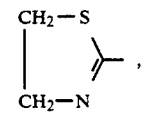

wherein
m is 1 or 2, Y is selected from the group consisting of —O—, —S—, —Se—, >CR$_2$R$_3$ wherein each of R$_2$ and R$_3$ is selected from the group consisting of —H and lower alkyl, each of Z$_2$, Z$_3$ and Z$_4$ is selected from the group consisting of
—H;
lower alkyl optionally substituted by any of —F, —Cl, —Br, —I and —NO$_2$;
lower alkoxy optionally substituted by any of —F, —Cl, —Br, —I and —NO$_2$;
aryl having 6 to 10 carbon atoms optionally substituted by any of —F, —Cl, —Br, —I, —NO$_2$, lower alkyl and lower alkoxy;
—NO$_2$;
—CF$_3$;
—N(R)$_2$ where R is lower alkyl;
—S—C$_6$H$_5$; and
—S(R')$_2$ where R' is lower alkyl; and wherein in said triphenylamine derivative at least 80% of the electrons in the highest occupied molecular orbital are located on the triphenylamine skeleton.

22. A photosensitive element according to claim 21 wherein X' is

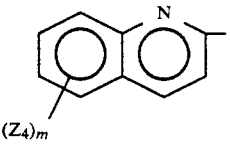

23. A photosensitive element according to claim 21 wherein X' is

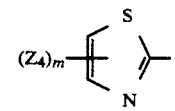

24. A photosensitive element according to claim 21 wherein said layer structure comprises a first layer containing said charge generating substance and a second layer containing said charge transport substance more remote from said substrate than said first layer.

25. A photosensitive element according to claim 21 wherein said layer structure comprises a layer containing said charge generating substance and said charge transport substance mixed.

26. A photosensitive element according to claim 21 further comprising a blocking layer lying between said layer structure containing said charge generating substance and said charge transport substance and said substrate.

27. A photosensitive element according to claim 21 wherein said layer structure comprises a charge transport layer containing said charge transport substance and a protective surface layer.

28. A photosensitive element according to claim 27 wherein said protective surface layer also contains said charge transport substance.

29. A photosensitive element according to claim 21 wherein said charge generating substance is a phthalocyanine compound.

30. A photosensitive element according to claim 21 which is in sheet form and wherein said substrate comprises a polymeric support sheet and a conductive thin film thereon.

31. Electrophotographic apparatus including at least one photosensitive element according to claim 21.

* * * * *